United States Patent [19]

Mueller, Jr.

[11] Patent Number: 4,775,371
[45] Date of Patent: Oct. 4, 1988

[54] STIFFENED DILATATION CATHETER AND METHOD OF MANUFACTURE

[75] Inventor: Richard L. Mueller, Jr., Mountain View, Calif.

[73] Assignee: Advanced Cardiovascular Systems, Inc., Mountain View, Calif.

[21] Appl. No.: 903,029

[22] Filed: Sep. 2, 1986

[51] Int. Cl.$^4$ .............................................. A61M 25/00
[52] U.S. Cl. .................... 604/280; 604/103; 604/98; 128/344
[58] Field of Search ............... 604/103, 280, 282, 22, 604/96, 97–102, 105, 106, 104; 128/344, 305, 303.17, 348.1

[56] References Cited

U.S. PATENT DOCUMENTS

| | | | |
|---|---|---|---|
| 4,239,042 | 12/1980 | Asai | 604/282 |
| 4,323,071 | 4/1982 | Simpson et al. | 604/98 |
| 4,563,181 | 1/1986 | Wijayarathna et al. | 604/280 |
| 4,571,240 | 2/1986 | Samson et al. | 604/280 |
| 4,581,390 | 4/1986 | Flynn | 604/280 |
| 4,597,755 | 7/1986 | Samson et al. | 604/103 |
| 4,636,346 | 1/1987 | Gold et al. | 604/280 |
| 4,702,252 | 10/1987 | Brooks et al. | 604/103 |

Primary Examiner—Stephen C. Pellegrino
Assistant Examiner—Colleen Reilly
Attorney, Agent, or Firm—Fulwider, Patton, Rieber, Lee & Utecht

[57] ABSTRACT

Stiffened dilation catheter and method of manufacturing the same. The catheter has a relatively stiff proximal end portion formed by bonding a relatively stiff tubular member coaxially within the proximal end portion of a relatively soft outer tubular member. The outer tubular member has a distensible portion which forms an inflatable balloon. An inner tubular member or shaft having an axial lumen adapted to receive a guide wire is positioned coaxially within the other tubular members. The distal end portions of the inner and outer tubular members are sealed together to close the distal end of the balloon, and an annular passageway for inflating and deflating the balloon is formed between the outer wall of the inner member and the inner wall of the stiffened proximal end portion of the outer tubular member. The relative wall thicknesses of the inner and outer tubular members can be varied to provide any desired stiffness or profile of stiffness along the length of the catheter.

6 Claims, 2 Drawing Sheets

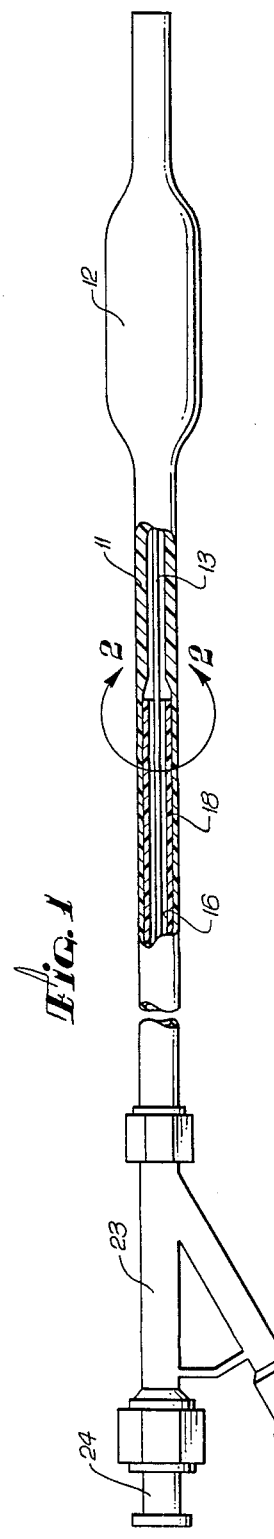
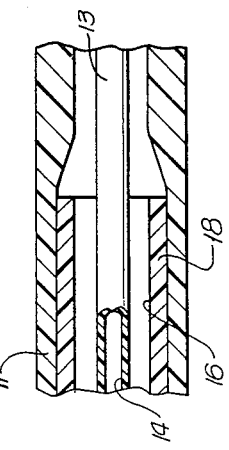
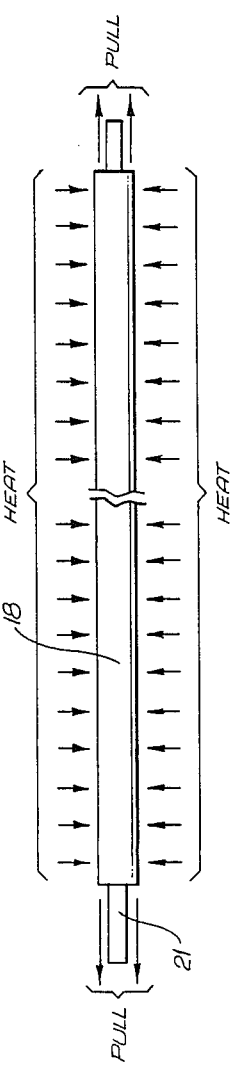
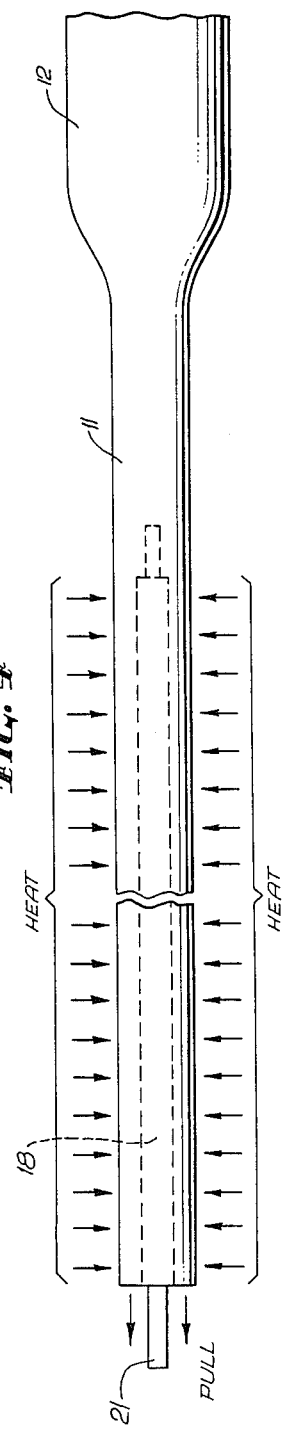

STIFFENED DILATATION CATHETER AND METHOD OF MANUFACTURE

This invention pertains generally to medical appliances, and more particularly to dilatation catheters for use in coronary angioplasty.

Dilatation balloon catheters are being made softer and with smaller profiles so they can track along guide wires and cross smaller lesions with less chance of injury to the patients. Unfortunately, as the catheters are made smaller and softer, they lose torsional and axial rigidity, and this makes it more difficult to steer the catheters along tortuous paths or to push them across tight lesions.

It is in general an object of the invention to provide a new and improved dilatation catheter and method of manufacturing the same.

Another object of the invention is to provide a dilatation catheter and method of the above character in which the catheter has good torsional and axial rigidity, with a soft tip formation safety.

These and other objects are achieved in accordance with the invention by providing a dilatation catheter having a relatively flexible tubular member with a relatively stiff tubular member affixed coaxially of the proximal end portion of the relatively flexible tubular member and extending a substantial portion of the length of the relatively flexible tubular member to provide torsional and axial rigidity for the proximal end portion of the relatively flexible tubular member without stiffening the relatively soft distal end portion of that member. The combined wall thickness of the relatively stiff tubular member and the proximal end portion of the relatively flexible tubular member is approximately equal to the wall thickness of the distal end portion of the relatively flexible tubular member. The relative wall thicknesses of the two members can be varied to provide any desired stiffness or profile of stiffness along the length of the catheter. In one disclosed embodiment, the relatively flexible tubular member has a distensible portion which forms an inflatable balloon beyond the distal end of the relatively stiff tubular member, and the distal end portion of an inner tubular member is bonded to the distal end portion of the relatively flexible tubular member to close the distal end of the balloon, with a passageway for inflating and deflating the balloon being formed between the outer wall of the inner tubular member and inner wall of the relatively stiff tubular member.

FIG. 1 is a side elevational view, partly broken away, of one embodiment of a dilatation catheter according to the invention.

FIG. 2 is an enlarged view of the area indicated by the line 2—2 in FIG. 1.

FIGS. 3 and 4 are side elevational views illustrating a preferred method of manufacturing the embodiment of FIG. 1.

Figure 5:
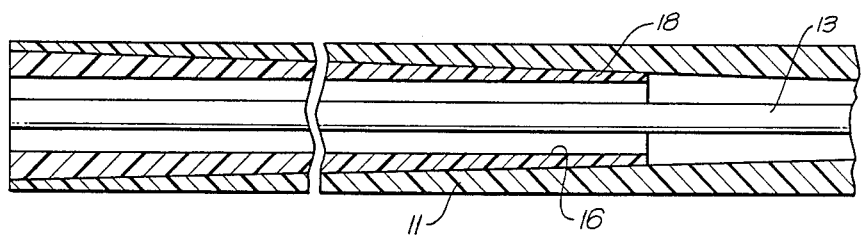
FIGS. 5-7 are fragmentary centerline sectional views of other embodiments of dilatation catheters according to the invention.

As illustrated in FIG. 1, the catheter comprises an axially elongated outer tubular member 11 having a distensible portion forming an inflatable balloon 12 near the distal end thereof. An inner tubular member or shaft 13 having an axially extending lumen 14 adapted to receive a guide wire (not shown) is positioned coaxially within the outer tubular member 11. The distal end portions of the tubular members are joined together by suitable means such as heat sealing to close the distal end of the balloon. An annular passageway 16 for inflating and deflating the balloon is formed between the proximal end portions of the tubular members in communication with the proximal end of the balloon.

A relatively stiff tubular member 18 is mounted coaxially within the proximal end portion of the outer tubular member 11 and affixed thereto. The relatively stiff tubular member extends a substantial portion (e.g., 25-95%) of the length of the outer tubular member, from the proximal end to a point near the balloon. In a typical catheter, the relatively stiff tubular member might, for example, extend for a distance on the order of 70-100 cm from the proximal end to a point on the order of 10-30 cm from the balloon.

The relatively stiff tubular member is fabricated of a material which is stiffer and more rigid than the relatively soft, flexible inner and outer tubular members. The inner and outer members can, for example, be fabricated of a low density polyethylene, and the relatively stiff tubular member can be fabricated of a high density polyethylene or a mixture of high density and low density polyethylene, e.g. 50% high density polyethylene and 50% low density polyethylene, or 75% high density polyethylene and 25% low density polyethylene. The relatively stiff member can also be fabricated of polypropylene or any other suitable material which is stiffer than the other tubular members. In the embodiment of FIG. 1, relatively stiff tubular member 18 and the proximal end portion of outer tubular member 11 have a combined wall thickness approximately equal to the wall thickness of the distal end portion of the outer tubular member. The distal end portion of the outer tubular member might, for example, have a wall thickness on the order of 0.005–0.006 inch, and the relatively stiff member and the proximal end portion of the outer tubular member might each have a wall thickness on the order of 0.002–0.003 inch. In this example, the relatively stiff tubular member and the distal end portion of the outer tubular member each might have a luminal opening on the order of 0.039 inch.

In one presently preferred method of manufacturing the embodiment of FIG. 1, outer tubular member 11 and relatively stiff tubular member 18 are each fabricated by extrusion with a wall thickness on the order of 0.006 inch. A Teflon beading mandrel 21 having a diameter on the order of 0.039 inch is inserted into the relatively stiff tubular member, and that tubular member is heated and pulled to shrink it down about the mandrel, thereby reducing the wall thickness of the member from about 0.006 inch to about 0.002–0.003 inch. Next, the outer tubular member is positioned over the relatively stiff member, and the proximal end portion of the outer tubular member is heated and shrunk about the relatively stiff tubular member. This reduces the wall thickness of the proximal end portion of the outer tubular member to about 0.002–0.003 inch and bonds the two tubular members together. Thereafter, the mandrel is removed, and the inner tubular member 13 is inserted into the luminal opening in the relatively stiff tubular member and the distal end portion of the outer tubular member. The distal end portions of the inner and outer tubular members are then heated and shrunk together to close the distal end of the balloon. The proximal end of the balloon remains open and in communication with the passageway 16 formed between the outer wall of the inner tubular member and the inner wall of the relatively stiff tubular member.

In operation and use, the catheter is connected to a two-arm adapter 23, as illustrated in FIG. 1. This adapter has a central port 24 which communicates with lumen 14 and a side port 26 which communicates with passageway 16. A guide wire (not shown) and/or contrast media can be inserted through port 24, and a fluid can be introduced and discharged through port 26 to inflate and deflate the balloon. As the catheter is inserted into the body, it can be pushed and twisted by means of the two-arm adapter and/or the catheter shaft itself to advance it over the guide wire and steer it through the vascular system to position the inflatable balloon 12 next to the lesion to be treated. The relatively stiff tubular member 18 gives the catheter a torsional rigidity and an axial rigidity which it otherwise would not have, thereby making it easier to push and turn the catheter as it is inserted. At the same time, the distal end portion of the catheter remains soft and flexible so that it will not harm the patient.

Figure 6:
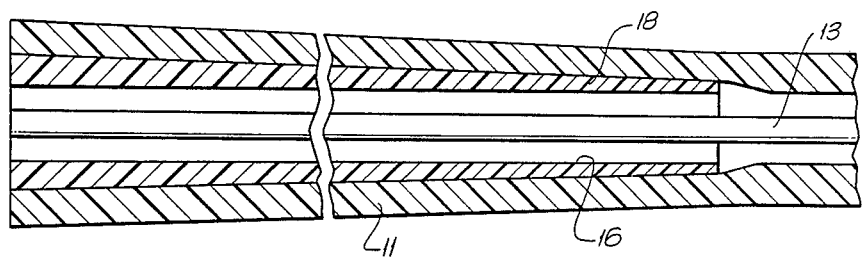
Figure 7:
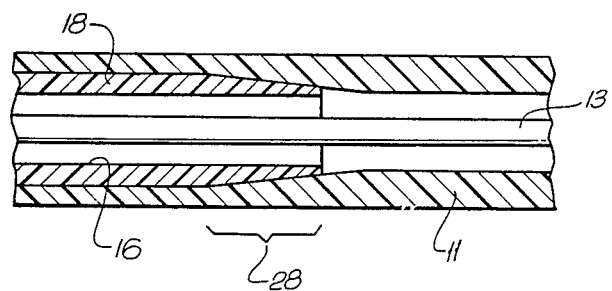

The embodiments illustrated in FIGS. 5–7 are generally similar to the embodiment of FIG. 1, and like reference numerals designate corresponding elements in all of these embodiments.

In the embodiment of FIG. 5, outer tubular member 11 and relatively stiff tubular member 18 are tapered in a complementary manner over the entire length of member 18. In this example, the distal end portion of the flexible tubular member 11 might have a wall thickness of 0.006 inch, tapering to a wall thickness of 0.001 inch at its proximal end, and the relative stiff tubular member might have a wall thickness of 0.005 inch at its proximal end, tapering to 0.001 inch at its distal end. At the distal end of member 18, outer member 11 might have a wall thickness on the order of 0.005 inch so that the combined wall thickness of the two tubular members is substantially uniform throughout the length of the catheter. With the relatively stiff tubular member tapering in this manner, the catheter is progressively stiffer toward its proximal end.

The embodiment of FIG. 5 can be manufactured in a manner similar to the method by which the embodiment of FIG. 1 is manufactured. Tubular members 11 and 18 are each fabricated by extrusion with a substantially uniform wall thickness of, for example, 0.006 inch. As in the previous method, relatively stiff tubular member 18 is shrunk about a Teflon beading mandrel of suitable diameter, e.g. 0.039 inch. In this embodiment, however, the heat and pulling force are progressively increased toward the distal end of the member to form the desired tapered. The outer tubular member is then positioned over the tapered relatively stiff member on the mandrel, and the proximal end portion of the outer tubular member is heated and shrunk with progressively less heat and pulling force toward the distal end of the relatively stiff tubular member to form the complementary taper. Thereafter, the mandrel is removed, and the process is completed in the manner described above.

In the embodiment of FIG. 6, relatively stiff tubular member 18 is tapered as in the embodiment of FIG. 5, but outer tubular member 11 has a substantially uniform wall thickness (e.g., 0.004 inch) throughout its length. Like the embodiment of FIG. 5, the embodiment of FIG. 6 is progressively stiffer toward the proximal end of the catheter.

The embodiment of FIG. 6 is manufactured by the same method as the embodiment of FIG. 5, except the heat and pulling force applied to the proximal end portion of outer tubular member 11 are substantially constant to produce the relatively uniform wall thickness.

In the embodiment of FIG. 7, outer tubular member 11 and inner tubular member 18 are tapered in a complementary manner in a transition region 28 near the distal end of the inner member. The remainder of the inner tubular member and the proximal end portion of the outer tubular member each have a substantially uniform wall thickness (e.g., 0.003 inch) throughout their length. In this example, the inner tubular member tapers to a thickness of 0.001 inch at its distal end, and the outer tubular member has a wall thickness on the order of 0.005 inch at this point. In this embodiment, the catheter has a substantially uniform thickness from its proximal end to the transition region 28 near the distal end of the inner tubular member.

The embodiment of FIG. 7 is manufactured by the same method as the embodiments of FIGS. 5 and 6. In this embodiment, however, the heat and pulling force are varied only in the transition region. They are maintained substantially constant elsewhere in order to provide the uniform wall thickness.

By varying the relative wall thicknesses of the relatively flexible and stiff tubular members, the catheter can be formed with any degree of stiffness or any stiffness profile desired.

The invention has a number of important features and advantages. It has the advantages of a small, soft catheter in that it can cross relatively tight lesions without harm to the patient. At the same time, it has an axial and torsional rigidity which makes it easier to advance and to steer in the vascular system. There is no perceptible bump or other discontinuity between the relatively stiff and relatively flexible portions of the catheter, and the manner in which the tubular members are pulled and shrunk enables them to have a substantially thinner wall thickness than would be possible if there were simply extruded. The outer balloon member maintains its integrity without a glue joint or a heat seal between two materials that could be effected by balloon inflation pressures. The catheter can be formed with any degree of stiffness or any stiffness profile desired.

It is apparent from the foregoing that a new and improved dilatation catheter and method of manufacturing the same have been provided. While only certain presently preferred embodiments have been described in detail, as will be apparent to those familiar with the art, certain changes and modifications can be made without departing from the scope of the invention as defined by the following claims.

I claim:

1. A dilatation catheter comprising an inner tubular member having an axially extending lumen for receiving a guide wire a relatively stiff intermediate tubular member, a relatively flexible outer tubular member disposed coaxially about the intermediate tubular member and shrunk-fit thereon, the outer tubular member having a distensible portion forming an inflatable balloon near the distal end thereof, the inner tubular member and the outer and intermediate tubular members defining an annular passageway for inflation fluid from the proximal ends thereof to the interior of the inflatable balloon, and the distal end portions of the inner and outer tubular members being sealed together to close the distal end of the balloon, the relatively stiff intermediate tubular member therefore extending distally from the proximal end of the outer tubular member for a distance of about 25–95% of the length of the outer tubular member.

2. The dilatation catheter of claim 1 wherein the combined wall thickness of the portion of the outer tubular member shrunk-fit onto the relatively stiff tubular member is approximately equal to the wall thickness of the distal end portion of the outer tubular member.

3. The dilatation catheter of claim 1 wherein the relatively stiff tubular member decreases in wall thickness toward the distal end of the catheter.

4. The dilatation catheter of claim 3 wherein the outer tubular member has a wall thickness which increases toward the distal end of the catheter.

5. The dilatation catheter of claim 1 wherein the outer tubular member is formed of polyethylene.

6. The dilatation catheter of claim 5 wherein the relatively stiff tubular member is formed from a polyethylene having a higher density than the polyethylene from which the outer tubular member is formed.

* * * * *